United States Patent [19]

Patton

[11] 4,164,938

[45] Aug. 21, 1979

[54] MEDICAL PRESSURE GAUGE AND INDICATOR DEVICE

[76] Inventor: William F. Patton, 1400 Edgewood, Ann Arbor, Mich. 48103

[21] Appl. No.: 854,870

[22] Filed: Nov. 25, 1977

[51] Int. Cl.$^2$ ............................................. A61B 10/00
[52] U.S. Cl. ..................................... 128/716; 73/731; 128/748
[58] Field of Search ............... 128/2 R, 2 A, 2 F, 2 G, 128/2.05 D, 2.05 E, 214.4, 262, 278, 351, DIG. 5; 116/114 PV, 124 R, DIG. 8, DIG. 9; 73/146.3, 146.8, 731

[56] References Cited

U.S. PATENT DOCUMENTS

| 1,448,728 | 3/1923 | Clotworthy | 116/DIG. 8 X |
| 3,785,367 | 1/1974 | Fortin et al. | 128/2 F |
| 3,890,842 | 6/1975 | Ramsey | 128/2.05 D X |
| 4,108,175 | 8/1978 | Orton | 128/214.4 |

FOREIGN PATENT DOCUMENTS 2516640 10/1976 Fed. Rep. of Germany ........... 128/262

OTHER PUBLICATIONS

Fig. 110–Edward's Vein Seeker, *Pye's Surgical Handicraft*, ed. by H. Bailey, Williams and Wilkens Co., Baltimore, Md., 16th ed., p. 48, 1950.

*Primary Examiner*—Richard T. Stouffer
*Attorney, Agent, or Firm*—Cullen, Sloman, Cantor, Grauer, Scott & Rutherford

[57] ABSTRACT

The medical pressure gauge and indicator device is for diagnosing the presence of tension pneumothorax in the pleural cavity of a patient. The gauge and indicator device comprises a diaphragm, a needle and a sleeve, with the diaphragm having an interior surface for contact with the pressurized air within the pleural cavity and having an exterior surface for contact with atmospheric air. The needle is of sufficient length for puncturing the chest wall and for extending into the pleural cavity. The sleeve is in the form of an elongated rigid tubular body, is provided with a pair of ends and mounts the needle and diaphragm at opposite ends thereof. The diaphragm has an expanded position and a collapsed position. When in the collapsed position, the diaphragm is generally located within the interior of the sleeve. The needle has a rear end inflow communication with the interior of the sleeve and the interior surface of the diaphragm and a sharpened chest wall-puncturing forward end. With such a construction, the needle is adapted to transmit the pressure of air within the pleural cavity to the interior of the sleeve where it acts upon the interior surface of the diaphragm, whereby, if a pressure greater than atmospheric pressure is present, the diaphragm will be urged out of the sleeve and form or assume a balloon-like shape or configuration which positively indicates the presence of greater than atmospheric air pressure within the pleural cavity, thus indicating to the medical person the treatment required for the patient. If the diaphragm does not expand, atmospheric or less than atmospheric pressure exits within the pleural cavity, thus indicating to the medical person another form of treatment required for the patient.

7 Claims, 2 Drawing Figures

MEDICAL PRESSURE GAUGE AND INDICATOR DEVICE

BACKGROUND OF THE PRESENT INVENTION

1. Field of the Invention

The pressure gauge and indicator device is to be used by trained medical personnel who normally work under emergency conditions where time is of the essence in determining the treatment required for a patient. A tension pneumothorax is a life-threatening condition requiring immediate treatment. Time does not normally permit X-raying of the patient. The medical person cannot always tell if greater than atmospheric air pressure is present in the pleural cavity. However, if there is a laceration or puncture wound of the lung region which allows air to enter and not to escape from the pleural cavity, the medical person needs to known such a condition immediately. The skilled medical person may be able to tell in certain cases by various known symptoms that a tension pneumothorax is present; however, the medical person wants to be completely sure of the aforementioned condition and to take positive steps to equilibrate the pressure to that of the atmosphere, if present in the pleural cavity.

2. Description of the Prior Art

The literature discloses the use of a technique or method for relieving the tension pneumothorax in a patient by using a syringe without a plunger, partly filled with sterile saline and having a needle thereon. The needle of the syringe is inserted into the patient's pleural cavity and the air leaking from the tension pneumothorax cavity can be seen as bubbles passing through the sterile saline. In the situation of a patient on a ventilator with a tension pneumothorax on initial insertion of the needle there will be continuous bubbling, indicating that there is tension in the pneumothorax cavity. As the tension decreases, bubbling may only be noticed on inspiration. There is usually no bubbling during expiration.

A search of the prior art resulted in the following United States Patents: Shiner, No. 3,319,622 of May 16, 1967; Portnoy et al, No. 3,322,114 of May 30, 1967; Mattson, No. 3,433,216 of Mar. 18, 1969; Summers No. 3,625,199 of Dec. 7, 1971; Chen, No. 3,731,691 of May 8, 1973; Fortin et al, No. 3,785,367 of Jan. 15, 1974; Jacobs, No. 3,794,026 of Feb. 26, 1974; Binard et al, No. 3,858,572 of Jan. 7, 1975; Steier, No. 3,895,533, of July 22, 1975; Dye et al, No. 3,920,002, of Nov. 18, 1975; Ogle, No. 3,942,514, of Mar. 9, 1976; Wiest, No. 3,982,533, of Sept. 28, 1976; Lyon et al, No. 4,027,661; of June 7, 1977. However, none of the prior art devices illustrate the efficient and fast acting device of the present invention.

SUMMARY OF THE INVENTION

It is a feature of the present invention to provide a medical pressure gauge and indicator device to aid in the diagnosis of tension pneumothorax.

A further feature of the present invention is to provide a disposable or throw-away medical pressure gauge and indicator device which is simple and inexpensive in construction, efficient in operation and is easy to manufacture and assemble.

A still further feature of the present invention is to provide a medical pressure gauge and indicator device which visually reports or indicates the positive pressure within the pleural cavity of a patient. This is accomplished by using an expandable diaphragm or balloon on one end of a rigid sleeve and a sharpened chest wall-puncturing needle on the other end of the sleeve.

Another feature of the present invention is to provide a medical pressure gauge and indicator device for diagnosing the presence of tension pneumothorax in the pleural cavity of a patient comprising a diaphragm having an interior surface for contact with the pressure of air within the pleural cavity and having an exterior surface for contact with atmospheric air. The device also includes a needle of sufficient length for puncturing the chest wall and for extending into the pleural cavity and an elongated rigid tubular sleeve having a pair of ends. The needle and the diaphragm are mounted on opposite ends of the sleeve. Means are provided for fixedly securing a portion of the diaphragm to one end of the sleeve, with the remaining portion of the diaphragm extending into the sleeve. The diaphragm has an expanded position and a collapsed position. The diaphragm when in the collapsed position is generally located within the interior of the sleeve. Adapter means are provided to mount the needle on the other end of the sleeve. The needle has a rear end inflow communication with the interior of the sleeve and with the interior surface of the diaphragm and a sharpened chest wall-puncturing forward end. The needle is adapted to transmit the pressure of air within the pleural cavity to the interior of the sleeve where it acts upon the interior surface of the diaphragm, whereby, if a pressure greater than atmospheric pressure is present, the diaphragm will be urged out of the sleeve and form a balloon-like shape which positively indicates to the medical person the presence of greater than atmospheric air pressure within the pleural cavity, thus indicating the kind of treatment required for the patient.

Still another feature is to provide a medical pressure gauge and indicator device of the aforementioned type whereby in operation and use, the non-expansion of the diaphragm indicates to the medical person that there is no tension pneumothorax present in the pleural cavity of the patient.

Other features of the medical pressure gauge and indicator device of the present invention include the use of a sleeve made from a plastic or from a plastic non-transparent material; a diaphragm which is relatively thin, made from a rubber or synthetic rubber-like material and having the shape of an elongated finger or of a balloon when in a collapsed condition within the sleeve; and the use of a fastening band for securing the turned over opened end of the finger-like diaphragm to the sleeve.

IN THE DRAWINGS

FIG. 1 is a pictorial view illustrating the insertion of the needle of the medical pressure gauge and indicator device through the chest wall of a patient into the pleural cavity, with the diaphragm in an expanded condition to indicate positive pressure and the presence of tension pneumothorax in the pleural cavity; and FIG. 2 is a longitudinal sectional view through the medical pressure gauge and indicator device, with the diaphragm shown in solid lines representing its collapsed position and the diaphragm shown in dotted lines representing its expanded position.

DESCRIPTION OF A PREFERRED EMBODIMENT

The practicing medical person is acquainted with the symptoms or signs tending to show that tension pneumothorax may exist in a patient. However, even knowing all the symptoms, a medical person cannot be completely accurate in his or her diagnosis at all times. Thus a more exacting technique requiring corresponding equipment is necessary.

Tension pneumothorax exists when the pressure in the pleural cavity is greater than that of the atmosphere. Various degrees of pneumothorax may occur following mechanical ventilation, tracheal inhalation, spontaneous rupture of an emphysematous bleb, cyst. Some may also occur in the presence of an apparently normal lung. Likewise, in the presence of an intact thorax, sharp fragments of fractured ribs may lacerate the lung surface with a similar result. In order for air to enter the pleural cavity from without, a communication between the atmosphere and the pleural space must exist. Often this is secondary to penetrating wounds, e.g., knife, bullet, thoracentesis attempts, subclavian vein puncture, etc. With a penetrating wound air may reach the pleural cavity also from the lung, if injury of the latter simultaneously occurs.

Minor degrees of pneumothorax may not create much difficulty. Severe alterations occur in tension pneumothorax. In order for tension pneumothorax to develop, there must exist a valvular mechanism, created usually by soft tissue adjoining the air leak, which allows air to enter the pleural cavity during inspiration more readily than it permits it to escape during expiration. The present invention is of considerable assistance to the medical person and will help to save time and lives.

The medical pressure gauge and indicator device is indicated by the numeral 10 and comprises an elongated, rigid, generally tubular body or sleeve 12 made from a plastic or plastic, non-transparent material, an elongated finger-shaped diaphragm or balloon 14 and an elongated needle 16.

Figure 1:
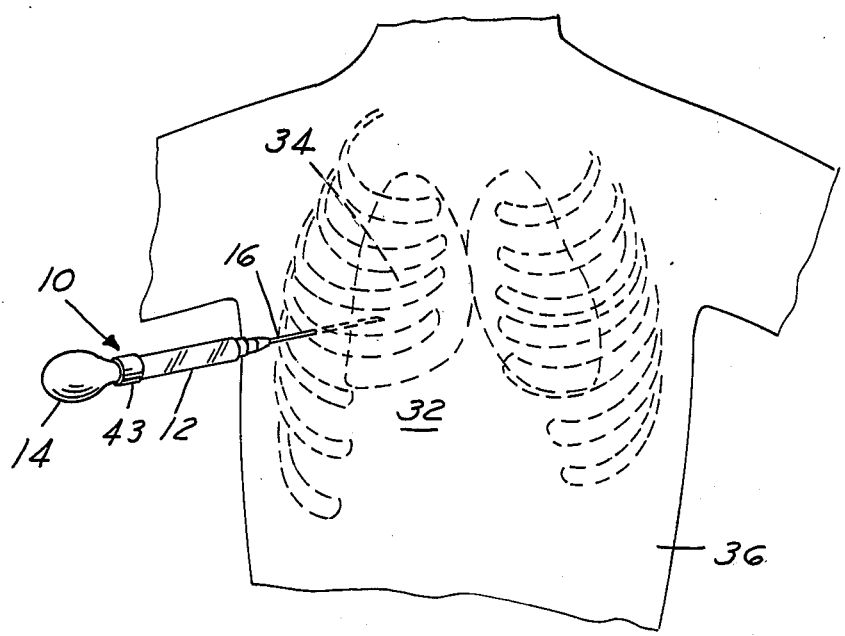

The needle 16 has a blunt rear end 18 extending into and carried by the cannula or adapter means 20 which has an axial passage 22 and an annular shoulder 24. The sleeve or body 12 has a pair of ends and is at one end reduced in diameter as indicated by the numeral 26. The reduced end portion 26 of sleeve 12 is provided on the inner periphery thereof with a pair of spaced annular ribs 28 and 30 for locating and fixedly positioning the shoulder 24 of the adapter means or cannula 20 therebetween. The elongated needle 16 also has a sharpened chest wall-puncturing forward end 30. The needle 16 is of sufficient length for puncturing the chest wall 32 and for extending into the pleural cavity 34 of the body 36 of a patient as shown in FIG. 1.

Figure 2:
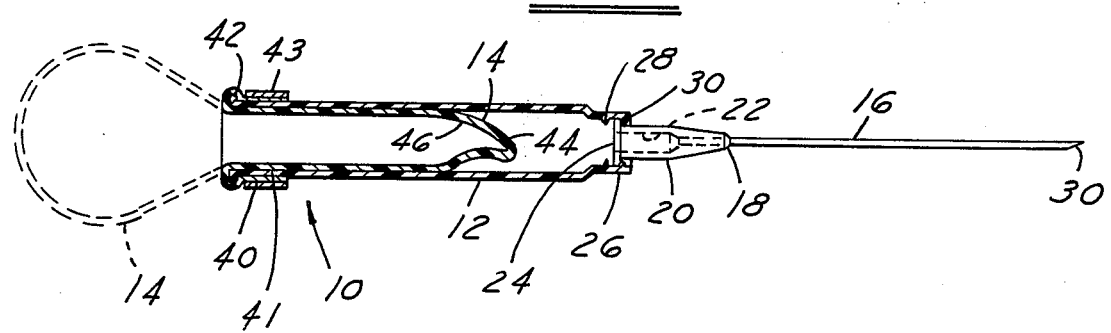

The finger-shaped diaphragm or balloon 14 is opened only at one end thereof, with the upper portion 40 of the diaphragm being turned over the annular shoulder or lip 42 provided at the end 41 of sleeve 12 as shown in FIG. 2. A circumferentially extending annular fastening band, ring or element 43 engages diaphragm portion 40 and fixedly secures the outer periphery or portion 40 of the diaphragm 14 to the end 41 of the sleeve 12 as shown in FIG. 2. The diaphragm 14 is relatively thin and is made from rubber or synthetic rubber-like material such as is used in hospital gloves. The diaphragm 14 when assembled in sleeve 12 has a length slightly less than the length of the sleeve 12 as shown in FIG. 2.

The diaphragm 14 has an interior surface 44 and an exterior surface 46 subjected to atmospheric pressure. When the diaphragm 14 is located within the interior of the sleeve 12 it is referred to herein as being in a collapsed position. When the diaphragm 14 is forced out of the sleeve 12 it is referred to herein as being in an expanded position.

The medical pressure gauge and indicator device 10 is of the disposable or throw-away type. No liquid or saline solution is required as is used in one prior art device described previously. Thus the problem of leakage of the saline solution is not present in this invention.

In use, the needle 16 of the medical pressure gauge and indicator device 10 is inserted by the medical person through the chest wall 32 into the pleural cavity 34. If a puncture or wound is present which permits air to enter the pleural cavity 34, the air escapes therefrom through the needle 16, cannula passage 22 into the interior of the sleeve 12 wherein it acts on the interior surface 44 of diaphragm 14 to urge same out of the sleeve 12 thus inflating the diaphragm or balloon 14 as shown in FIG. 1. The needle 16 thus transmits the pressure of air within the pleural cavity to the interior of the sleeve 12 where it acts upon the interior surface 44 of the diaphragm 14, whereby, if a pressure greater than atmospheric pressure is present the diaphragm 14 will be urged out of the sleeve 12 and form a balloon-like shape or configuration which positively and visually indicates to the medical person the presence of air, caused by a puncture or wound, affecting the pleural cavity 34. Thus, by the inflation of the diaphragm 14, the medical person knows the treatment to follow since tension pneumothorax is present in the patient. If the diaphragm 14 is not inflated, the medical person knows what other treatment, if any, is required.

What is claimed is:

1. A medical pressure gauge and indicator device for diagnosing the presence of tension pneumothorax in the pleural cavity of a patient comprising a diaphragm having an interior surface for contact with the pressure of air within the pleural cavity and having an exterior surface for contact with atmospheric air: a needle of sufficient length for puncturing the chest wall and for extending into the pleural cavity; an elongated rigid tubular sleeve having a pair of ends and mounting said needle and said diaphragm; means for fixedly securing a portion of said diaphragm to one end of said sleeve, with the remaining portion of said diaphragm extending into said sleeve; said diaphragm having an expanded position and a collapsed position; said diaphragm when in said collapsed position being generally located within the interior of said sleeve; said diaphragm when in said expanded position being located outside of said sleeve; adapter means mounting said needle on the other end of said sleeve; said needle having a rear end inflow communication with the interior of said sleeve and the interior surface of said diaphragm and a sharpened chest wall-puncturing forward end; said needle being adapted to transmit the pressure of air within the pleural cavity to the interior of said sleeve where it acts upon the interior surface of said diaphragm, said diaphragm forming pressure means whereby, if a pressure greater than atmospheric pressure is present, the diaphragm will be urged out of said sleeve to said expanded position and will form a balloon-like shape which positively indicates the presence of greater than atmospheric air within the pleural cavity, thus indicating the treatment required for the patient.

2. The medical pressure gauge and indicator device as defined in claim 1 wherein said diaphragm is elongated and is opened at one end thereof, said diaphragm at the opened end thereof being located exteriorly of said sleeve and being turned over said one end of said sleeve; and a fastening band surrounding said exterior portion of the diaphragm for fixedly mounting same to said sleeve.

3. The medical pressure gauge and indicator device as defined in claim 1 wherein said sleeve is made from a plastic material.

4. The medical pressure gauge and indicator device as defined in claim 1 wherein said sleeve is made from a plastic non-transparent material.

5. The medical pressure gauge and indicator device as defined in claim 1 wherein said diaphragm is relatively thin and is made from rubber or a synthetic rubber-like material.

6. The medical pressure gauge and indicator device as defined in claim 1 wherein said device is disposable after use.

7. The medical pressure gauge and indicator device as defined in claim 1 wherein said diaphragm in its collapsed state has a configuration like a finger of a glove, and has a length less than the length of said sleeve.

* * * * *